United States Patent
Im et al.

(10) Patent No.: US 9,622,986 B2
(45) Date of Patent: Apr. 18, 2017

(54) PERCUTANEOUS ABSORPTION PREPARATION CONTAINING DONEPEZIL, AND METHOD FOR PREPARING SAME

(71) Applicant: SK CHEMICALS CO., LTD., Gyeonggi-do (KR)

(72) Inventors: Jong-Seob Im, Gyeonggi-do (KR); Yong-Youn Hwang, Gyeonggi-do (KR); Won-No Youn, Seoul (KR); Yeo-Jin Park, Seoul (KR); Hye-Min Kim, Gyeonggi-do (KR); Joon-Gyo Oh, Gyeonggi-do (KR); Hun-Taek Kim, Seoul (KR); Bong-Yong Lee, Seoul (KR)

(73) Assignee: SK Chemicals Co., Ltd., Seongnam-si, Gyeonggi-do (KR)

( * ) Notice: Subject to any disclaimer, the term of this patent is extended or adjusted under 35 U.S.C. 154(b) by 0 days.

(21) Appl. No.: 14/381,627

(22) PCT Filed: Feb. 26, 2013

(86) PCT No.: PCT/KR2013/001504
§ 371 (c)(1),
(2) Date: Aug. 28, 2014

(87) PCT Pub. No.: WO2013/129813
PCT Pub. Date: Sep. 6, 2013

(65) Prior Publication Data
US 2015/0045749 A1 Feb. 12, 2015

(30) Foreign Application Priority Data
Feb. 28, 2012 (KR) .................. 10-2012-0020510

(51) Int. Cl.
*A61K 9/70* (2006.01)
*A61K 31/445* (2006.01)

(52) U.S. Cl.
CPC .......... *A61K 9/7084* (2013.01); *A61K 9/7053* (2013.01); *A61K 9/7061* (2013.01); *A61K 9/7069* (2013.01); *A61K 31/445* (2013.01)

(58) Field of Classification Search
CPC .. A61K 31/445; A61K 9/7053; A61K 9/7061; A61K 9/7069; A61K 9/7084
USPC .......................... 427/2.31; 604/307; 424/484
See application file for complete search history.

(56) References Cited

U.S. PATENT DOCUMENTS

| | | | |
|---|---|---|---|
| 7,858,114 B2 | 12/2010 | Ito | |
| 2004/0258741 A1 | 12/2004 | Terahara et al. | |
| 2007/0259028 A1 | 11/2007 | Ito | |
| 2008/0038328 A1 | 2/2008 | Higo et al. | |
| 2009/0175929 A1 | 7/2009 | Terahara et al. | |
| 2010/0178307 A1* | 7/2010 | Wen | A61K 31/445 424/400 |
| 2011/0059141 A1 | 3/2011 | Ito | |
| 2011/0066120 A1* | 3/2011 | Lee | A61F 13/02 604/290 |

FOREIGN PATENT DOCUMENTS

CA 2804148 A1 * 1/2012 ........... A61K 9/7061

* cited by examiner

*Primary Examiner* — Janet Epps-Smith
*Assistant Examiner* — Courtney Brown
(74) *Attorney, Agent, or Firm* — Vorys, Sater, Seymour & Pease LLP; Mih Suhn Koh

(57) ABSTRACT

Provided is a transdermal delivery system (for example, in the form of a patch) having a double-layer structure including a drug-containing matrix layer and an adhesive layer, wherein the drug-containing matrix layer is obtained by completely dissolving donepezil using a certain polymer and then formulating along with an adhesive; and a process for preparing the same. The transdermal delivery system according to the present invention does not show any crystallization of donepezil in the formulation, can release donepezil at a uniform rate for a long time, and can inhibit the release dumping phenomenon that occurs in a transdermal delivery system having a single-layer structure.

13 Claims, 3 Drawing Sheets

PERCUTANEOUS ABSORPTION PREPARATION CONTAINING DONEPEZIL, AND METHOD FOR PREPARING SAME

TECHNICAL FIELD

The present invention relates to a donepezil-containing transdermal delivery system and a process for preparing the same. More specifically, the present invention relates to a transdermal delivery system (for example, in the form of a patch) having a double-layer structure including a drug-containing matrix layer and an adhesive layer, wherein the drug-containing matrix layer is obtained by completely dissolving donepezil using a certain polymer and then formulating along with an adhesive; and a process for preparing the same.

BACKGROUND ART

Donepezil or its salt, whose chemical name is 2-[(1-benzyl-4-piperidinyl)methyl]-5,6-dimethoxyindan-1-one, is an acetylcholinesterase inhibitor used as a therapeutic agent for treating dementia.

Dementia occurs primarily in the elderly. Elderly people often have difficulty in swallowing and a lot of patients suffering from fairly advanced dementia also have difficulty in taking an oral formulation. In addition, in case of oral administration, plasma drug concentrations may increase and decrease very rapidly, which results in causing side effects. Therefore, there is a need for formulations capable of maintaining a plasma concentration uniformly and continuously. For example, EP1437130A1 has disclosed a transdermal delivery system containing an antidementia agent such as donepezil. The transdermal delivery system has a structure in which the antidementia agent such as donepezil is dispersed in an adhesive; and is designed so as to maintain the plasma drug concentration uniformly for more than 12 hours when applied to the skin. And also, WO2007/129427 has disclosed a transdermal delivery system having a triple-layer structure including an adhesive layer, a drug-containing layer, and an intermediate layer.

Meanwhile, for normal patients suffering from dementia, it is necessary to design a transdermal delivery system capable of maintaining the blood concentration of a drug for 1 day to several days, e.g., for more than 1 day, preferably for more than about 1 week. Such a transdermal delivery system requires using relatively high amounts of a drug, e.g., donepezil. However, if the amount of donepezil is increased in conventional transdermal delivery systems, donepezil become crystallized in the formulations, thereby causing problems such as reduction in the adhesive strength. Furthermore, in case of the transdermal delivery system of a triple-layer form designed to control the release rate of donepezil, the production process thereof become complicated and difficult; and there are disadvantages such as poor economic efficiency.

In addition, even when a transdermal delivery system acting for a long time is designed through completely dissolving donepezil with a conventional solubilizing agent such as surfactants, rapid release dumping phenomenon occurs during the use thereof. Therefore, it is required to design a transdermal delivery system capable of inhibiting the release dumping problems effectively.

DISCLOSURE

Technical Problem

The present inventors have found that a transdermal delivery system (for example, in the form of a patch) having a double-layer structure including a drug-containing matrix layer and an adhesive layer wherein the drug-containing matrix layer is obtained by completely dissolving donepezil using a certain polymer, i.e., polyvinylpyrrolidone, and then formulating along with an adhesive can release donepezil at a uniform rate for a long time, e.g., for more than 1 day, preferably for more than about 1 week, and can inhibit the release dumping phenomenon.

Therefore, it is an object of the present invention to provide said transdermal delivery system having a double-layer structure.

It is another object of the present invention to provide a process for preparing said transdermal delivery system.

Technical Solution

In accordance with an aspect of the present invention, there is provided a transdermal delivery system consisting of a backing layer, a drug-containing matrix layer, an adhesive layer and a release layer, wherein the drug-containing matrix layer comprises (i) donepezil or a pharmaceutically acceptable salt thereof as an active ingredient, (ii) polyvinylpyrrolidone, and (iii) an acrylic adhesive; and wherein the adhesive layer comprises an acrylic adhesive or a silicone adhesive.

In the transdermal delivery system of the present invention, the drug-containing matrix layer may comprise 10 to 40% by weight of donepezil or its pharmaceutically acceptable salt, 0.1 to 20% by weight of polyvinylpyrrolidone, and 40 to 80% by weight of the acrylic adhesive, based on the total weight of the drug-containing matrix layer; preferably, 30 to 40% by weight of donepezil or its pharmaceutically acceptable salt, 1 to 20% by weight of polyvinylpyrrolidone, and 40 to 60% by weight of the acrylic adhesive, based on the total weight of the drug-containing matrix layer. And also, the polyvinylpyrrolidone may have a weight-average molecular weight ranging from 7,000 to 1,500,000.

In an embodiment, the adhesive layer may comprise a silicone adhesive and have a thickness ranging from 50 to 150 μm, preferably 90 to 110 μm.

In accordance with another aspect of the present invention, there is provided a process for preparing a transdermal delivery system, the process comprising (a) dissolving an acrylic adhesive in a solution containing donepezil or a pharmaceutically acceptable salt thereof and polyvinylpyrrolidone; (b) casting the solution obtained in step (a) on a film, followed by drying, to form a drug-containing matrix layer; and (c) forming an adhesive layer comprising an acrylic adhesive or a silicone adhesive on the drug-containing matrix layer obtained in step (b).

The solution containing donepezil or a pharmaceutically acceptable salt thereof and polyvinylpyrrolidone may be obtained by mixing a mixture of donepezil or a pharmaceutically acceptable salt thereof and ethyl acetate with a solution of polyvinylpyrrolidone in ethanol.

Advantageous Effects

The transdermal delivery system having a double-layer structure according to the present invention does not show any crystallization of donepezil in the formulation, can release donepezil at a uniform rate for a long time, and can inhibit the release dumping phenomenon that occurs in a transdermal delivery system having a single-layer structure. Especially, when the drug-containing matrix layer and the adhesive layer are respectively formulated by using different adhesives, the release of donepezil can be controlled at a uniform rate for more than 1 week, along with inhibiting release dumping phenomena. And also, the transdermal delivery system having a double-layer structure according to the present invention can minimize contacting between air (oxygen) and donepezil, which also contributes to the stability thereof. Therefore, the transdermal delivery system according to the present invention can be usefully applied to dementia patients, especially elderly patients, without incurring the side effects according to rapid increase of a blood concentration.

BEST MODE

Figure 1:
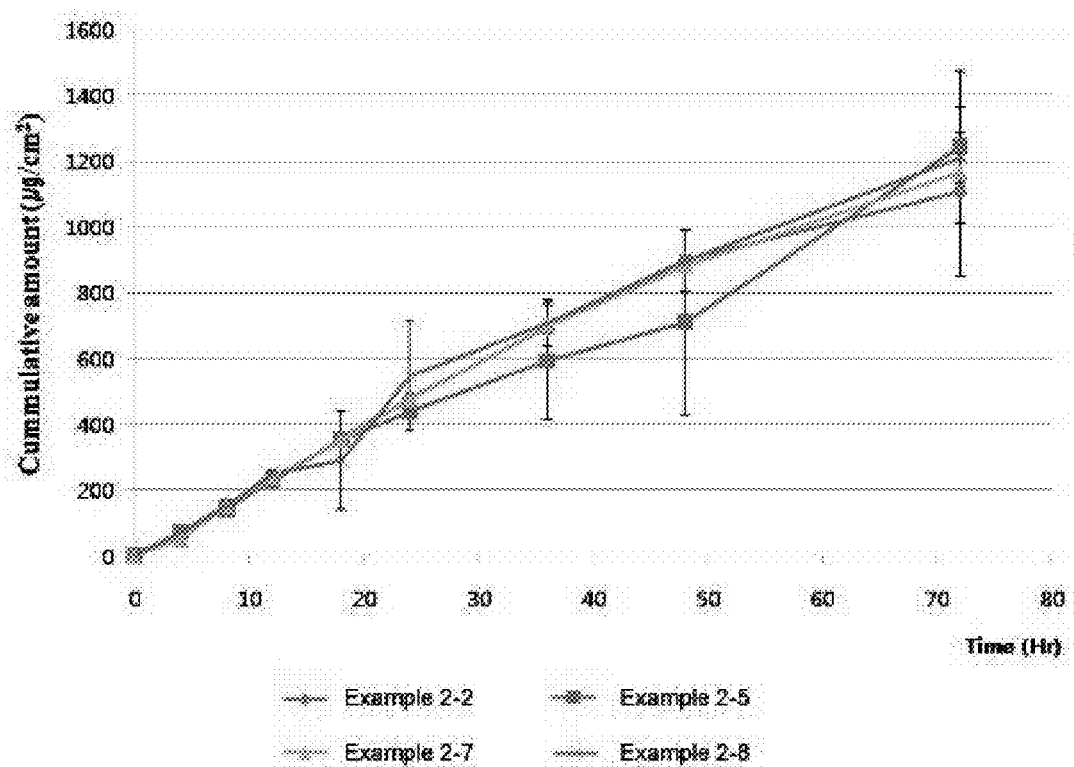
FIG. 1 shows the evaluation results on in vitro skin penetration rates of the transdermal delivery systems prepared by using polyvinylpyrrolidones having various weight-average molecular weights.

The present invention provides a transdermal delivery system consisting of a backing layer, a drug-containing matrix layer, an adhesive layer and a release layer, wherein the drug-containing matrix layer comprises (i) donepezil or a pharmaceutically acceptable salt thereof as an active ingredient, (ii) polyvinylpyrrolidone, and (iii) an acrylic adhesive; and wherein the adhesive layer comprises an acrylic adhesive or a silicone adhesive.

In the transdermal delivery system according to the present invention, the donepezil or its pharmaceutically acceptable salt (e.g., donepezil hydrochloride) may be used in an amount sufficient to obtain a therapeutically effective blood concentration, for example, in an amount ranging from 10 to 40% by weight, preferably from 30 to 40% by weight, based on the total weight of the drug-containing matrix layer. If the amount of donepezil or its pharmaceutically acceptable salt is less than 10% by weight, desired therapeutic effects may not be obtained. If the amount of donepezil or its pharmaceutically acceptable salt is more than 40% by weight, adhesive strength may be reduced; and drug crystals may be formed.

The polyvinylpyrrolidone increases the solubility of donepezil and thus plays a role in enabling the complete dissolution of donepezil in the transdermal delivery system. Said polyvinylpyrrolidone may have a weight-average molecular weight ranging from 7,000 to 1,500,000; and may be used in an amount ranging from 0.1 to 20% by weight, preferably 1 to 20% by weight, more preferably 4 to 12% by weight, based on the total weight of the drug-containing matrix layer. If the amount of polyvinylpyrrolidone is less than 0.1% by weight, desired solubilizing effects may not be obtained. If the amount of polyvinylpyrrolidone is more than 20% by weight, the drug-containing matrix layer is discolored; or the resulting very high viscosity may make the formulation process difficult.

The acrylic adhesive is a polymer having adhesiveness, which has a carboxyl group, a hydroxyl group, or a combination thereof as a functional group. The examples thereof include Durotak 87-202A, Durotak 387-2510, Durotak 87-4287, Durotak 387-2287, Durotak 87-2287, Durotak 387-2516, Durotak 87-2516, Durotak 387-2525, Durotak 87-2525, Durotak 87-2979, Durotak 87-2074, Durotak 87-235A, Durotak 87-2353, Durotak 387-2353, Durotak 87-2852, Durotak 87-2051, Durotak 387-2051, Durotak 87-2052, Durotak 387-2052, Durotak 387-2054, Durotak 87-2054, Durotak 87-2677, Durotak 87-2194, Durotak 387-2196, Durotak 387-2825, Durotak 87-2825, Durotak 87-502A, Durotak 87-503A, Durotak 87-504A, etc. Preferably, the acrylic adhesive may be Durotak 87-2516 (Henkel), Durotak 87-235A (Henkel), Durotak 87-2353 (Henkel), Durotak 387-2353 (Henkel), or Durotak 87-502A (Henkel). The acrylic adhesive may be used in an amount ranging from 40 to 80% by weight, preferably 40 to 60% by weight, based on the total weight of the drug-containing matrix layer.

In an embodiment, the drug-containing matrix layer may comprise 10 to 40% by weight of donepezil or its pharmaceutically acceptable salt, 0.1 to 20% by weight of polyvinylpyrrolidone, and 40 to 80% by weight of the acrylic adhesive, based on the total weight of the drug-containing matrix layer. In another embodiment, the drug-containing matrix layer may comprise 30 to 40% by weight of donepezil or its pharmaceutically acceptable salt, 1 to 20% by weight of polyvinylpyrrolidone, and 40 to 60% by weight of the acrylic adhesive, based on the total weight of the drug-containing matrix layer.

If necessary, the drug-containing matrix layer may further comprise a plasticizer or a stabilizer. The plasticizer or the stabilizer may be used in an amount of about 40% by weight or less, based on the total weight of the drug-containing matrix layer, but is not limited thereto.

The transdermal delivery system according to the present invention includes an adhesive layer comprising an acrylic adhesive or a silicone adhesive.

The acrylic adhesive is the same as described in the above.

The silicone adhesive is a polymer having both compatibility with drugs having an amine group and adhesiveness. The examples thereof include BIO-PSA 7-4301, BIO-PSA 7-4302, BIO-PSA 7-4303, BIO-PSA 7-4201, BIO-PSA 7-4202, BIO-PSA 7-4302, BIO-PSA 7-4101, BIO-PSA 7-4102, BIO-PSA 7-4103, etc. Preferably, the silicone adhesive may be BIO-PSA 7-4302 (Dow corning), BIO-PSA 7-4202 (Dow corning), or BIO-PSA 7-4102 (Dow corning).

Meanwhile, it has been found that when the drug-containing matrix layer and the adhesive layer are respectively formulated by using different adhesives, the release of donepezil can be controlled at a uniform rate for more than 1 week, along with inhibiting release dumping phenomena. Therefore, in an embodiment of the present invention, the adhesive layer comprises a silicone adhesive preferably. And also, the thickness thereof may be 50 to 150 μm, preferably 90 to 110 μm, more preferably about 100 μm.

The present invention also provides a process for preparing a transdermal delivery system, the process comprising (a) dissolving an acrylic adhesive in a solution containing donepezil or a pharmaceutically acceptable salt thereof and polyvinylpyrrolidone; (b) casting the solution obtained in step (a) on a film, followed by drying, to form a drug-containing matrix layer; and (c) forming an adhesive layer comprising an acrylic adhesive or a silicone adhesive on the drug-containing matrix layer obtained in step (b).

In step (a), the solution containing donepezil or a pharmaceutically acceptable salt thereof and polyvinylpyrrolidone may be obtained by mixing a mixture of donepezil or a pharmaceutically acceptable salt thereof and ethyl acetate with a solution of polyvinylpyrrolidone in ethanol.

Step (b) may be performed by casting the solution obtained in step (a) on a film, followed by drying, to form a drug-containing matrix layer. The film may be a conventional PET film, for example a PET film coated with silicone. The drying may be performed by drying in a about 70° C. oven for 15 minutes. And also, a conventional backing film, for example a polyester film laminated with aluminum, may be laminated on the opposite side to the film (i.e., on the side to which the drug-containing matrix layer is exposed) to form a backing layer. In addition, flexible materials impermeable to drug conventionally used in the field of a transdermal delivery system may be used as the backing film. For example, there may be used polyolefin, polyether, a multi-layer ethylene vinyl acetate film, polyester, polyurethane, etc.

Step (c) may be performed by forming an adhesive layer comprising an acrylic adhesive or a silicone adhesive on the drug-containing matrix layer obtained in step (b). The adhesive layer containing a silicone adhesive may be formed by casting the silicone adhesive on for example a fluorine-coated PET film in a predetermined thickness, drying in a about 70° C. oven for about 15 minutes, and then laminating the resulting adhesive layer on the drug-containing matrix layer obtained in step (b). And also, the adhesive layer containing an acrylic adhesive may be formed by casting the acrylic adhesive on for example a silicone-coated PET film in a predetermined thickness, drying in a about 70° C. oven for about 15 minutes, and then laminating the resulting adhesive layer on the drug-containing matrix layer obtained in step (b).

A release layer may be formed on the formulation having a backing layer, a drug-containing matrix layer, and an adhesive layer obtained as in the above to prepare a transdermal delivery system in the form of a patch. For the release layer, conventional release liners or their laminates used in the field of a transdermal delivery system may be used. For example, there may be used a film, a paper, or a laminates thereof, which made of polyethylene, polyester, polyvinyl chloride, polyvinylidene chloride, etc. coated with silicone resin or fluoride resin.

The present invention will be described in further detail with reference to the following examples. These examples are for illustrative purposes only and are not intended to limit the scope of the present invention.

EXAMPLE 1

Evaluation of Polymers

Preliminary experiments were performed for evaluating the compatibilities between various polymers and adhesives. We evaluated the effects of the polymers having relatively good compatibility, which found from the preliminary experiments, on the solubilization of donepezil base. That is, donepezil (1 g) and ethyl acetate (1 g) were mixed each other. In separate vessels, other polymers (each being 0.2 g), i.e., polyvinylpyrrolidone (PVP K17, BASF), Eudragit™ E100 (Degussa), and Plastoid™ B (Evonik Industries AG), were dissolved in ethanol (0.8 g) to obtain the solutions, which were then respectively added to the mixed solution of donepezil and ethyl acetate. In case of the 1-1 (no polymer added), ethanol (1.0 g) was added to the mixed solution of donepezil and ethyl acetate. Each of the solutions was stirred for 2 hours, and then the results obtained by observing each appearance are shown in Table 1 below.

TABLE 1

| | | 1-1 | 1-2 | 1-3 | 1-4 |
|---|---|---|---|---|---|
| Law material | Donepezil base | 1 g | 1 g | 1 g | 1 g |
| Solvent 1 | Ethyl acetate | 1 g | 1 g | 1 g | 1 g |
| Polymer | Polyvinyl-pyrrolidone | — | 0.2 g | — | — |
| | Eudragit E100 | — | — | 0.2 g | — |
| | Plastoid B | — | — | — | 0.2 g |
| Solvent 2 | Ethanol | 1 g | 0.8 g | 0.8 g | 0.8 g |
| Appearance of solution | | Opaque | Transparent | Opaque | Opaque |

From the results of Table 1, it can be seen that, when polyvinylpyrrolidone is used, donepezil is completely dissolved to show transparent appearance. Accordingly, it was concluded that said polyvinylpyrrolidone having compatibility with an adhesive increases the solubility of donepezil effectively, thereby being especially suitable as a solubilizing agent for donepezil.

EXAMPLE 2

Evaluation of Formulations According to Molecular Weights of Polyvinylpyrrolidone The effect of molecular weight of polyvinylpyrrolidone on formulating a transdermal delivery system was evaluated. Solutions containing donepezil base and polyvinylpyrrolidone were prepared in the same procedures as in Example 1, according to the compositions of Table 2 below (in case of the 2-1, only ethanol (1 g) was added thereto). An acrylic adhesive was added to the solutions, which were then homogenized. Each resulting solution was casted on a PET film coated with silicone. Each resulting film was dried in a 70° C. oven for 15 minutes and then laminated with a backing film. The formulation potentiality thereof was evaluated. In Table 2, PVP K17 (weight-average molecular weight: 7,000 to 11,000, BASF), PVP K30 (weight-average molecular weight: 44,000 to 54,000, BASF), or PVP K90 (weight-average molecular weight: 1,000,000 to 1,500,000, BASF) was used as the polyvinylpyrrolidone; and Durotak 87-235A (Henkel) was used as the acrylic adhesive.

TABLE 2

| | | 2-1 | 2-2 | 2-3 | 2-4 | 2-5 | 2-6 | 2-7 | 2-8 |
|---|---|---|---|---|---|---|---|---|---|
| Law material | Donepezil base (g) | 1 | 1 | 1 | 1 | 1 | 1 | 1 | 1 |
| Solvent 1 | Ethyl acetate (g) | 2 | 2 | 2 | 2 | 2 | 2 | 2 | 2 |
| Polymer | PVP K17 (g) | — | 0.2 | 0.4 | 0.6 | — | — | — | — |
| | PVP K30 (g) | — | — | — | — | 0.2 | 0.4 | 0.6 | — |
| | PVP K90 (g) | — | — | — | — | — | — | — | 0.2 |
| Solvent 2 | Ethanol | 1 | 0.8 | 0.6 | 0.4 | 0.8 | 0.6 | 0.4 | 0.8 |
| Adhesive | Acrylic adhesive (g) | 3.5 | 3.5 | 3.5 | 3.5 | 3.5 | 3.5 | 3.5 | 3.5 |
| | Total (g) | 7.5 | 7.5 | 7.5 | 7.5 | 7.5 | 7.5 | 7.5 | 7.5 |

The solution 2-1 which contains no polymer showed very low viscosity and thus could not be casted on the film. As can be seen from the above results, it is preferable that polyvinylpyrrolidone has a weight-average molecular weight ranging from 7,000 to 1,500,000; and that it is used in an amount ranging about 1 to 20% by weight, more preferably 4 to 12% by weight.

FIG. 1 shows the evaluation results on in vitro skin penetration rates of the transdermal delivery systems prepared in Examples 2-2, 2-5, 2-7, and 2-8. The skin penetration rates were determined as follows: Each transdermal delivery system was cut so as to have a size of 1 cm² and then attached on the human cadaver skin. The sample diffused through the skin was automatically collected at predetermined times. The internal temperature of the Franz cell was set to 32.5° C.; and a phosphate buffer having pH 7.4 was used as a test medium. The collected samples were analyzed with high performance liquid chromatography. From the results of FIG. 1, it can be seen that each transdermal delivery system shows uniform flux values.

EXAMPLE 3

Preparation and Evaluation of Transdermal Delivery Systems Having a Double-Layer Structure (1) Preparation of Transdermal Delivery Systems The transdermal delivery systems were prepared according to the compositions shown in Table 3 below and then the in vitro skin penetration rates thereof were evaluated. In Table 3, PVP K90 (BASF) was used as the polyvinylpyrrolidone; Durotak 87-235A (Henkel) was used as the acrylic adhesive; and Bio-PSA 7-4302 (Dow corning) was used as the silicone adhesive.

(2) Evaluation of in vitro Skin Penetration Rates

The in vitro skin penetration rates of the transdermal delivery systems of Examples 3-1 to 3-4 were evaluated with a Franz cell (vertical diffusion cell). The skin penetration rates were determined as follows: Each transdermal delivery system was cut so as to have a size of 1 cm² and then attached on the human cadaver skin. The sample diffused through the skin was automatically collected at predetermined times. The internal temperature of the Franz cell was set to 32.5° C.; and a phosphate buffer having pH 7.4 was used as a test medium. The collected samples were analyzed with high performance liquid chromatography. The results are shown in FIG. 2.

Figure 2:
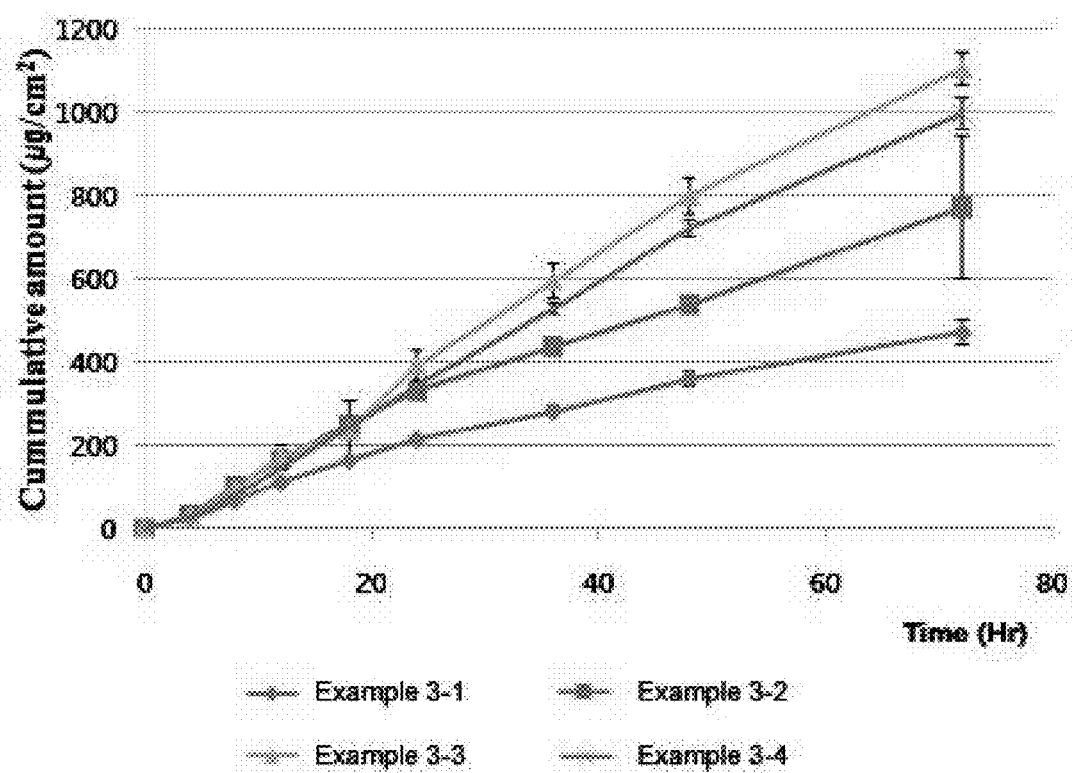
FIG. 2 shows the evaluation results on in vitro skin penetration rates of the transdermal delivery system having a double-layer structure according to the present invention.

As shown in the results of FIG. 2, the transdermal delivery systems having the adhesive layer consisting of the same acrylic adhesive as used in the drug-containing matrix layer (i.e., Examples 3-3 and 3-4) showed relatively rapid release patterns of donepezil; and therefore it is expected that they can be usefully used as a relatively short-acting transdermal delivery system (for example, about 72 hour-acting transdermal delivery system). On the other hand, the transdermal delivery systems having the adhesive layer consisting of the

TABLE 3

| | | | Example | | | |
|---|---|---|---|---|---|---|
| | | | 3-1 | 3-2 | 3-3 | 3-4 |
| Drug-containing matrix layer | Active ingredient | Donepezil base (g) | 1 | 1 | 1 | 1 |
| | Solvent 1 | Ethyl acetate (g) | 2 | 2 | 2 | 2 |
| | Polymer | Polyvinylpyrrolidone (g) | 0.2 | 0.2 | 0.2 | 0.2 |
| | Solvent 2 | Ethanol (g) | 0.8 | 0.8 | 0.8 | 0.8 |
| | Adhesive | Acrylic adhesive (g) | 3.5 | 3.5 | 3.5 | 3.5 |
| Adhesive layer | Type of adhesive | | Silicone adhesive | Silicone adhesive | Acrylic adhesive | Acrylic adhesive |
| | Thickness after drying | | 100 μm | 50 μm | 100 μm | 50 μm |

The drug-containing matrix layer (thickness: 65 μm), in which donepezil base, polyvinylpyrrolidone, and the acrylic adhesive were casted on a PET film coated with silicone, was prepared in the same procedures as in Example 2, according to the components and amounts shown in Table 3. The resulting drug-containing matrix layer was laminated with a polyester backing film laminated with aluminum to form a first layer.

The silicon adhesive (BIO-PSA-7-4302, Dow corning) was casted on a fluorine-coated PET film so as to give a thickness after drying of 100 μm (Example 3-1) or 50 μm (Example 3-2), followed by drying in a 70° C. oven for 15 minutes to form a skin-adhesive layer (a second layer). From the first layer prepared in the above, the silicone-coated PET film was peeled off. The resulting first layer was laminated with each second layer to prepare the transdermal delivery systems of Examples 3-1 and 3-2.

And also, The acrylic adhesive, which is the same acrylic adhesive as used in the drug-containing matrix layer, was casted on a silicone-coated PET film so as to give a thickness after drying of 100 μm (Example 3-3) or 50 μm (Example 3-4), followed by drying in a 70° C. oven for 15 minutes to form a skin-adhesive layer (a second layer). From the first layer prepared in the above, the silicone-coated PET film was peeled off. The resulting first layer was laminated with each second layer to prepare the transdermal delivery systems of Examples 3-3 and 3-4.

silicone adhesive (i.e., Examples 3-1 and 3-2) showed controlled-release patterns of donepezil. Especially, the transdermal delivery systems, in which the adhesive layer has a thickness of 100 μm, showed excellent controlled-release patterns of donepezil. Therefore, it is expected that they can be usefully used as a long-acting transdermal delivery system (for example, about 1 week-acting transdermal delivery system)

(3) In vivo Evaluation of Transdermal Delivery Systems

The long-acting controlled-release characteristics of the transdermal delivery system of Example 3-1 were evaluated using hairless rats. For comparison, a transdermal delivery system having a single layer structure (Comparative Example 1) was also evaluated. The transdermal delivery system of Comparative Example 1 was prepared by forming a drug-containing matrix layer (thickness: 65 μm) in the same procedures as in Example 2-8, except for using 0.5 g of donepezil base and 2.5 g of ethyl acetate.

The transdermal delivery system of Comparative Example 1 was cut so as to have a size of 10 cm². The transdermal delivery system of Example 3-1 was cut so as to have sizes of 5 cm² and 10 cm². After each transdermal delivery system was attached on hairless rats, the blood samples were collected at 2, 4, 6, 12, 24, 48, 72, 96, 120, 144, and 168 hour, i.e., for 168 hours (1 week); and then each amount of donepezil in the plasma was determined. The blood concentration-time profiles are shown in FIG. 3.

Figure 3:
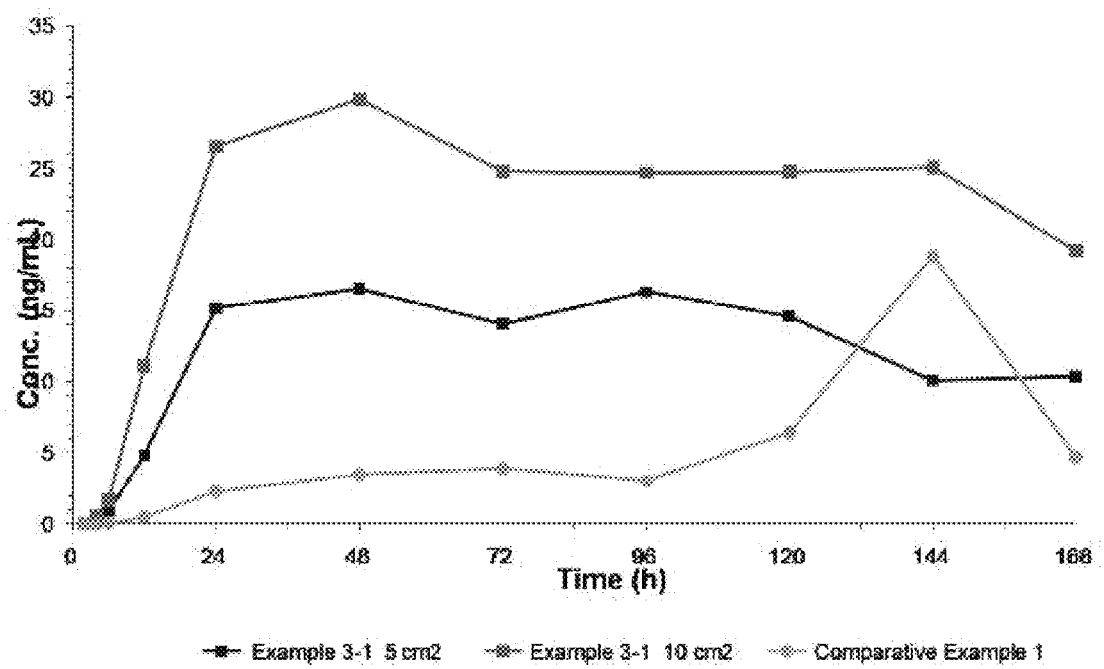
FIG. 3 shows the results obtained by measuring in vivo drug concentration profiles of the transdermal delivery systems of the present invention and the comparative formulation for 1 week.

As shown in the results of FIG. 3, the transdermal delivery system having a single layer structure of Comparative Example 1 showed low blood concentrations and then the unexpected release dumping phenomenon at the time of 144 hours. However, the transdermal delivery systems of a double layer structure having sizes of 5 cm$^2$ and 10 cm$^2$ showed significant controlled-release profiles of donepezil along with maintaining the therapeutically effective concentrations for one week, where the reduction to a half of the drug amount leads to the reduction to a half of the drug concentration in the blood. Therefore, it can be seen that the transdermal delivery systems having a double layer structure according to the present invention can release donepezil uniformly and continuously for a long time.

The invention claimed is:

1. A transdermal delivery system consisting of:
   a backing layer,
   a drug-containing matrix layer,
   a drug-free adhesive layer, and
   a release layer,
   wherein the drug-containing matrix layer comprises: (i) donepezil or a pharmaceutically acceptable salt thereof as an active ingredient, (ii) polyvinylpyrrolidone, and (iii) an acrylic adhesive,
   the drug-free adhesive layer comprises a silicone adhesive, and
   the drug release is controlled by the drug-containing matrix and the drug-free adhesive layer.

2. The transdermal delivery system of claim 1, wherein the drug-containing matrix layer comprises 10 to 40% by weight of donepezil or its pharmaceutically acceptable salt, 0.1 to 20% by weight of polyvinylpyrrolidone, and 40 to 80% by weight of the acrylic adhesive, based on the total weight of the drug-containing matrix layer.

3. The transdermal delivery system of claim 2, wherein the drug-containing matrix layer comprises 30 to 40% by weight of donepezil or its pharmaceutically acceptable salt, 1 to 20% by weight of polyvinylpyrrolidone, and 40 to 60% by weight of the acrylic adhesive, based on the total weight of the drug-containing matrix layer.

4. The transdermal delivery system of claim 1, wherein the polyvinylpyrrolidone has a weight-average molecular weight ranging from 7,000 to 1,500,000.

5. The transdermal delivery system of claim 1, wherein the adhesive layer has a thickness ranging from 50 to 150 μm.

6. The transdermal delivery system of claim 1, wherein the adhesive layer has a thickness ranging from 90 to 110 μm.

7. A process for preparing a transdermal delivery system, the process comprising
   (a) dissolving an acrylic adhesive in a solution containing donepezil or a pharmaceutically acceptable salt thereof and polyvinylpyrrolidone;
   (b) casting the solution obtained in step (a) on a film, followed by drying, to form a drug-containing matrix layer; and
   (c) forming a drug-free adhesive layer comprising a silicone adhesive on the drug-containing matrix layer obtained in step (b)
   wherein the drug release is controlled by the drug-containing matrix formed in (b) and the drug-free adhesive layer formed in (c).

8. The process for preparing a transdermal delivery system of claim 7, wherein the solution containing donepezil or a pharmaceutically acceptable salt thereof and polyvinylpyrrolidone is obtained by mixing a mixture of donepezil or a pharmaceutically acceptable salt thereof and ethyl acetate with a solution of polyvinylpyrrolidone in ethanol.

9. The process for preparing a transdermal delivery system of claim 7, wherein the drug-containing matrix layer comprises 10 to 40% by weight of donepezil or its pharmaceutically acceptable salt, 0.1 to 20% by weight of polyvinylpyrrolidone, and 40 to 80% by weight of the acrylic adhesive, based on the total weight of the drug-containing matrix layer.

10. The process for preparing a transdermal delivery system of claim 9, wherein the drug-containing matrix layer comprises 30 to 40% by weight of donepezil or its pharmaceutically acceptable salt, 1 to 20% by weight of polyvinylpyrrolidone, and 40 to 60% by weight of the acrylic adhesive, based on the total weight of the drug-containing matrix layer.

11. The process for preparing a transdermal delivery system of claim 7, wherein the polyvinylpyrrolidone has a weight-average molecular weight ranging from 7,000 to 1,500,000.

12. The process for preparing a transdermal delivery system of claim 7, wherein the forming an adhesive layer is performed so as to obtain the adhesive layer having a thickness ranging from 50 to 150 μm.

13. The process for preparing a transdermal delivery system of claim 7, wherein the forming an adhesive layer is performed so as to obtain the adhesive layer having a thickness ranging from 90 to 110 μm.

* * * * *